US006914170B2

(12) United States Patent
Li et al.

(10) Patent No.: US 6,914,170 B2
(45) Date of Patent: Jul. 5, 2005

(54) METHODS FOR REGULATING BETA-OXIDATION IN PLANTS

(75) Inventors: Chun Ping Li, Johnston, IA (US);
Peizhong Zheng, Johnston, IA (US);
Scott E. Nichols, Westchester, PA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 335 days.

(21) Appl. No.: 09/899,645

(22) Filed: Jul. 5, 2001

(65) Prior Publication Data

US 2002/0078475 A1 Jun. 20, 2002

Related U.S. Application Data

(60) Provisional application No. 60/216,211, filed on Jul. 6, 2000.

(51) Int. Cl.$^7$ .......................... C12N 15/29; C12N 15/52; C12N 15/82; A01H 5/00; A01H 5/10
(52) U.S. Cl. ........................ 800/281; 800/278; 800/298; 800/320; 800/320.1; 800/320.2; 800/320.3; 435/418; 435/468
(58) Field of Search ................................ 800/278, 281, 800/298, 320, 320.1, 320.2, 320.3, 286; 435/419, 468, 320.1, 465; 536/23.1, 23.2, 23.6

(56) References Cited

U.S. PATENT DOCUMENTS 6,677,502 B1 * 1/2004 Allen et al. .................. 800/278

FOREIGN PATENT DOCUMENTS

| EP | 0 894 864 A1 | 2/1999 |
| EP | 1 033 405 A2 | 9/2000 |
| WO | WO 97/43422 A1 | 11/1997 |
| WO | WO 98/06831 A1 | 2/1998 |
| WO | WO 99/45122 A1 | 9/1999 |
| WO | WO 02/08433 A2 | 1/2002 |

OTHER PUBLICATIONS

Harwood, J. L. et al. Biochemica et Biophysica Acta, 1996; vol. 1301; pp. 7–56.*
Eccleston V. et al., The Plant Cell, Apr. 1998, vol. 10; pp. 613–621.*
Walbot V.; GenBank accession number AI600977 entered into the public database on Apr. 13, 1999.*
Gordon–Kamm W. et al. The Plant Cell. Jul. 1990, vol. 2, pp. 603–618.*
Cases, S., et al., "Identification of a Gene Encoding an Acyl CoA:Diacylglycerol Acyltransferase, a Key Enzyme in the Triacylglycerol Synthesis," Proc. Natl. Sci. USA, Oct. 1998, pp. 13018–13023, vol. 95, The National Academy of Sciences.

Chang, C., et al., "Metabolic Control of Peroxisome Abundance," Journal of Cell Science, 1999, pp. 1579–1590, vol. 112, The Company of Biologists Limited, Great Britain.
Jones, J., et al., "Identification of Peroxisomal Acyl–CoA Thioesterases in Yeast and Humans," Journal of Biological Chemistry, Apr. 1999, pp. 9216–9223, vol. 274 (14), The American Society for Biochemistry and Molecular Biology, Inc.
Harwood, J., "Recent Advances in the Biosynthesis of Plant Fatty Acids", Biochimica et Biophysica Acta, 1996, pp. 7–56, vol. 1301, Elsevier Science B.V.
Smith, S., "The Animal Fatty Acid Synthase; One Gene, One Polypeptide, Seven Enzymes," FASEB Journal, 1994, pp. 1248–1259, vol. 8 (15).
GenBank Report for Accession No. AF078752, Direct Submission on Jul. 16, 1998.
GenBank Report for Accession No. BAA83582, Direct Submission on Aug. 25, 1999.
GenBank Report for Accession No. AF124264, Direct Submission on Jan. 27, 1999.
GenBank Report for Accession No. AF124265, Direct Submission on Jan. 27, 1999.
Chang, C., et al., "Metabolic Control of Peroxisome Abundance," Journal of Cell Science, Apr. 1999, vol. 112, pp. 1579–1590, The Company of Biologists Limited, Great Britain.
Eccleston, V., et al., "Medium–Chain Fatty Acid Biocynthesis and Utilization in Brassica napus Plants Expressing Lauroyl–acyl Carrier Protein Thioesterase," Planta, 1996, pp. 46–53, Springer–Verlag.
Eccleston, V. and J. Ohlrogge, "Expression of Lauroyl–Acyl Carrier Protein Thioesterase in Brassica napus Seeds Induces Pathways for Both Fatty Acid Oxidation and Biosynthesis and Implies a Set Point for Triacylglycerol Accumulation," The Plant Cell, Apr. 1998, vol. 10, pp. 613–621, American Society of Plant Physiologists, USA.
Jones, J., et al. ., "Identification of Peroxisomal Acyl–CoA Thioesterases in Yeast and Humans," The Journal of Biological Chemistry, Apr. 1999, vol. 274(14), pp. 9216–9223, The American Society for Biochemistry and Molecular Biology, Inc., USA.

(Continued)

Primary Examiner—Phuong T. Bui
Assistant Examiner—Russell Kallis
(74) Attorney, Agent, or Firm—Alston & Bird LLP

(57) ABSTRACT

The invention relates to the genetic manipulation of plants to increase oil accumulation in plant tissues, particularly seeds. Methods for decreasing β-oxidation in plants and optimizing oil accumulation in a seeds are provided. The methods find use in increasing the accumulation of oil or particular oil constituents in plant seeds. Isolated nucleotide molecules, isolated proteins, expression cassettes and transformed plants, plant tissues and plant cells are additionally provided.

19 Claims, No Drawings

OTHER PUBLICATIONS

Safford, R., et al., "Regulated Expression of the Rat Medium Chain Hydrolase Gene in Transgenic Rape Seed," *Transgenic Research*, 1993, vol. 2, pp. 191–198, Chapman & Hall, UK.

Biosis Database Report for Accession No. PREV197967018097, 1978 (XP002201237).

EMBL Database Report for Accession No. AC009273, Aug. 13, 1999 (XP002201236).

EMBL Database Report for Accession No. AW453228, Feb. 21, 2000 (XP002201235).

EMBL Database Report for Accession No. AW459595, Mar. 2, 2000 (XP002201777).

SWISPROT Database Report for Accession No. AL161472, Mar. 16, 2000 (XP002201779).

SWISPROT Database Report for Accession No. O65261, Aug. 1, 1998 (XP002201778).

* cited by examiner

US 6,914,170 B2

METHODS FOR REGULATING BETA-OXIDATION IN PLANTS

CROSS REFERENCE TO RELATED APPLICATIONS

This application claims the benefit of U.S. Provisional Application No. 60/216,211, filed Jul. 6, 2000; which is hereby incorporated herein in its entirety by reference.

FIELD OF THE INVENTION

The invention relates to the genetic manipulation of plants, particularly to altering lipid metabolism in plants and plant seeds.

BACKGROUND OF THE INVENTION

Vegetable oil, particularly oil extracted from seeds, is an important agricultural commodity. Currently, most of the vegetable oil that is produced is directly or indirectly consumed by humans. Because the oxidation of vegetable oils can lead to undesirable odors and flavors in the oil that consumers find unpalatable, agricultural scientists initiated efforts to improve the oxidative stability of vegetable oils. The scientists have significantly improved this aspect of oil quality. The oxidative stability of the vegetable oil is primarily related to the number of double bonds in its fatty acids. That is, fatty acids with several double bonds are known to be more unstable than fatty acids with fewer double bonds. Thus, scientists have worked to improve shelf life and oxidative stability by reducing the amount of the trienoic fatty acid, α-linolenic acid.

Other work has concentrated on producing oils with specific fatty acid compositions. Recently, medical science has provided evidence that the replacement of fats in the human diet with oils rich in the monounsaturated fatty acid, oleic acid, is beneficial to human cardiovascular health. Medical and nutritional experts alike are now advocating the replacement of fats in the human diet with oils rich in the monounsaturated fats. As a result of the increased demand for oils rich in monounsaturated fatty acids, agricultural scientists have concentrated their efforts on developing new plant varieties for the production of vegetable oils that are rich in oleic acid. High-oleic canola (*Brassica* spp.), safflower, and sunflower oils are now available.

More recently, agricultural scientists have initiated efforts to genetically engineer crop plants to produce seed oils containing unusual fatty acids, such as epoxy and hydroxy fatty acids. Primarily, scientists have initiated these efforts to produce oil containing such fatty acids for use in industrial applications. Such fatty acids find use as plasticizers, lubricants, surfactants, components of paints and renewable raw materials in a myriad of industrial syntheses. One goal of the scientists is to develop renewable replacements for the non-renewable, petroleum-based, raw materials upon which industry currently depends. Thus, in the future, vegetable oils with unusual fatty acids are likely to increase in industrial importance as the world's finite petroleum reserves diminish.

While some progress has been made in the genetic engineering of crop plants for the production of seed oils with unusual fatty acids, agricultural scientists have experienced difficulties in achieving levels of these fatty acids that make the industrial use of the oil economically practical. The challenge remains for agricultural scientists to increase the levels of the these fatty acids in the seeds of crop plants used for oil production.

SUMMARY OF THE INVENTION

Compositions and methods are provided for decreasing β-oxidation in plants. The compositions comprise nucleotide sequences encoding acyl-CoA thioesterases, particularly maize peroxisomal acyl-CoA thioesterases. The compositions find use in methods for modulating acyl-CoA levels in a plant. The compositions and methods find use in increasing the level of oil in a plant or part thereof by reducing the rate of fatty acid catabolism, particularly β-oxidation, in peroxisomes. The methods involve modulating the level of an acyl-CoA thioesterase in a plant, particularly in peroxisomes. By increasing or decreasing the level of the acyl-CoA thioesterase in the peroxisome, the level of CoASH is altered, causing a decline in β-oxidation.

Methods for optimizing a plant for seed oil production are also provided. Such methods involve increasing or decreasing the level of an acyl-CoA thioesterase in plant peroxisomes and also involve decreasing the level or activity of one or more additional proteins in a plant which affect β-oxidation either directly or indirectly. Such additional proteins may be enzymes involved directly in β-oxidation or proteins that control peroxisome biogenesis and abundance.

Transformed plants, plant tissues and plant cells, and seeds thereof are provided. Additionally provided are isolated proteins comprising acyl-CoA thioesterases.

DETAILED DESCRIPTION OF THE INVENTION

The invention is drawn to compositions and methods for altering lipid metabolism in plants. Particularly, the invention provides compositions and methods for decreasing βoxidation in plants and plant seeds. By decreasing β-oxidation in plant tissues that accumulate oil, such as, for example, developing seeds and fruits, increased accumulation of oil or constituents of the oil can be achieved in a plant or part thereof. Thus, the compositions and methods of the invention find use in increasing in a plant, or part thereof, the accumulation of oil and/or the level of particular constituents of the oil. The compositions and methods find further use in increasing the accumulation of unusual fatty acids, or triacylglycerols comprising at least one unusual acyl chain, in plants.

The invention provides compositions comprising isolated nucleotide molecules which comprise nucleotide sequences encoding acyl-CoA thioesterases, particularly maize acyl-CoA thioesterases, more particularly maize peroxisomal acyl-CoA thioesterases. The invention further provides expression cassettes comprising such nucleotide sequences and isolated proteins encoded by such nucleotide sequences.

Acyl-CoA thioesterase catalyzes the hydrolysis of an acyl-CoA to a free fatty acid and CoASH. Acyl CoA-thioesterases are found in the cytosol, mitochondria, and peroxisomes in yeast and animal cells (Smith (1994) *FASEB J* 8:1248–1259). Recently, acyl-CoA thioesterase has been implicated in controlling fatty acid β-oxidation in fungi. In a strain of yeast possessing a deletion mutation of the gene encoding a peroxisomal acyl-CoA thioesterase, growth of the strain on a medium containing fatty acids is impaired relative to the growth of a wild-type strain on the same medium. (Jones et al. (1999) *J. Biol Chem.* 274:9216–9223). Interestingly, overexpression of the peroxisomal acyl-CoA thioesterase gene can also lead to reduced β-oxidation. Recently, Chang et al. ((1999) *J. Cell Sci.* 112:1579–1590) demonstrated that in human skin fibroblasts which had been genetically manipulated to overexpress peroxisomal acyl-CoA thioesterase had a reduced peroxisome abundance.

Because the peroxisomes are one of the sites of β-oxidation in human cells, a decrease in peroxisome abundance in such cells is likely to be correlated with a decrease in β-oxidation. The combined results from yeast and human skin fibroblasts indicate that an optimal level of acyl-CoA thioesterase is essential to maintaining a normal rate of β-oxidation in a cell. The combined results also indicate that abnormally high or low levels of acyl-CoA thioesterase can perturb metabolic processes or peroxisome abundance, resulting in a decreased flux of carbon through the β-oxidation pathway.

Methods are provided for modulating acyl-CoA thioesterase expression in a plant. The methods find use in modulating acyl-CoA thioesterase expression in a plant or part thereof. By "modulating acyl-CoA thioesterase expression" is intended decreasing or increasing the level of acyl-CoA transcripts, protein, enzyme activity or combination thereof. The methods of the invention employ the acyl-CoA thioesterase nucleotide sequences of the invention. The methods involve transforming at least one cell of a plant with at least a portion of: a nucleotide sequence set forth in SEQ ID NO: 1, a nucleotide sequence comprising at least 45% identity to the nucleotide set forth in SEQ ID NO: 1, or a nucleotide sequence encoding the amino acid sequence set forth in SEQ ID NO: 2.

The methods of the invention do not depend on a particular method of transforming a plant or cell thereof with a nucleotide construct. Any method for transforming a plant with a nucleotide construct known in the art may be employed in the methods of the invention including stable, transient and virus-mediated transformation methods. If expression of the acyl-CoA thioesterase nucleotide sequence is desired in a plant, the nucleotide construct may additionally comprise a promoter that drives expression in a plant cell. Such a promoter is operably linked to the nucleotide sequence of the invention for the production of either sense or antisense transcripts. Preferred methods of the invention additionally involve regenerating the transformed cell into a transformed plant.

Promoters of interest are seed-preferred, embryo-preferred, constitutive, chemically regulatable, tissue-preferred, and developmentally regulated promoters. Preferred promoters of the invention are seed-preferred and embryo-preferred promoters.

If desired, the level of thioesterase transcripts, or protein or enzyme activity may be assessed to determine if the desired change in acyl-CoA thioesterase expression has been achieved. Methods for assessing transcripts, proteins and acyl-CoA thioesterase are known in the art. Transcripts may be assessed by, for example, northern blot analysis or RNase protection assays, and acyl CoA thioesterase protein may be determined by, for example, western blotting. Acyl-CoA thioesterase activity may be determined by enzyme activity assays.

Methods are provided for decreasing β-oxidation in a plant. Such methods find use in increasing the level of oil or the level of a constituent of the oil in a plant or part thereof. Generally, plants tissues do not accumulate substantial levels of oil. However, certain plant species have tissues, particularly in seeds and fruits, that accumulate substantial amounts of oil. Preferred plant parts or tissues of the invention are seeds, embryos and fruits. In seeds that produce oil, the oil is primarily synthesized during seed development. As oil synthesis proceeds in the developing seed, the predominant pathway for lipid degradation in plants, β-oxidation, is also operable. Thus, the accumulation of oil within a developing seed can be decreased because of β-oxidation. Reduced carbon in the form of fatty acids and their derivatives can be shunted from oil synthesis to β-oxidation, resulting in a reduced accumulation of oil. The present invention provides methods that can increase the level of oil, or at least one constituent of the oil, synthesized in a plant or part thereof. Such methods involve decreasing β-oxidation by modulating acyl-CoA thioesterase expression in a plant.

While the invention does not depend on any particular biological mechanism, decreasing acyl-CoA thioesterase expression may reduce β-oxidation by reducing the rate of production of CoASH. Because a fatty acid must be esterified with CoASH to form fatty acyl-CoA before β-oxidation, limiting the formation of CoASH will reduce fatty acyl-CoA production, and thus decrease β-oxidation. Alternatively, increasing or overexpressing acyl-CoA thioesterase is known to reduce peroxisome abundance. Because the peroxisome a major site of β-oxidation in plant tissues, a decrease in peroxisome abundance in a cell is likely to decrease the flux of carbon to β-oxidation.

The methods for decreasing β-oxidation involve modulating acyl-CoA thioesterase expression, particularly peroxisomal acyl-CoA thioesterase expression. The methods do not depend on a particular method of modulating acyl-CoA thioesterase expression in a plant. Any method known in the art for modulating expression may be employed singly or in combination to achieve the desired result. It is recognized that acyl-CoA thioesterase expression in a plant may be affected by genetically manipulating a plant to increase or decrease the level of acyl-CoA thioesterase protein produced. For example, an increase in acyl-CoA thioesterase protein may be achieved by transforming the plant with a nucleotide construct comprising a promoter that drives expression in a plant cell operably linked to a nucleotide sequence encoding an acyl-CoA thioesterase. Alternatively, acyl-CoA thioesterase expression may be affected by modifying the kinetic properties of an endogenous acyl-CoA thioesterase through site-directed alterations of the coding sequence of the endogenous gene resulting in changes in the amino acid sequence of the encoded enzyme. Such site-directed alterations may be accomplished by any method known in the art including, but not limited to, a chimeraplasty-based method involving a nucleotide construct of the invention. In yet another approach, acyl-CoA thioesterase expression may be decreased or increased by administering to a plant allosteric effectors or enzyme activity inhibitors of the thioesterase. Preferably, such effectors or inhibitors are administered to a plant before or during oil synthesis in the plant. Additionally, modulating the level in a cell of one or more specific proteins, other than or in addition to, an acyl-CoA thioesterase, can alter acyl-CoA thioesterase in the cells. Human HIV-Nef protein, for example, is known to enhance the activity of a peroxisomal acyl-CoA thioesterase, PTE1, by a mechanism with involves the binding of Nef to PTE1 (Watanabe et al. (1997) *Biochim. Biophys. Res Comm.* 238: 234–239.

Preferably acyl-CoA thioesterase expression is modulated in a plant by transforming the plant or plant cell with at least a portion of an acyl-CoA thioesterase nucleotide sequence. By "acyl-CoA thioesterase nucleotide sequence" is intended any nucleotide sequence of an acyl-CoA thioesterase gene or transcript, including, but not limited to, coding sequences, exons, introns, 5'-regulatory regions, 3'-regulatory regions, 5'-untranslated regions, 3'-untranslated regions and the like. Any acyl-CoA thioesterase nucleotide sequences known in the art may be employed in the methods of the present invention. Preferred acyl-CoA thioesterases nucleotide sequences are those which encode peroxisomal acyl-CoA thioesterases. More preferred acyl-CoA thioesterase nucleotide sequences include the nucleotide sequence set forth in SEQ ID NO: 1, a nucleotide sequence comprising at least 45% identity to the nucleotide set forth in SEQ ID NO: 1, a nucleotide sequence encoding the amino acid sequence set forth in SEQ ID NO: 2 and the nucleotide sequences set forth in GenBank Accession Nos. AF124264 (SEQ ID NO: 3) and AF124265 (SEQ ID NO: 5). Most preferred acyl-CoA thioesterases nucleotide sequences include the nucleotide sequence set forth in SEQ ID NO: 1, a nucleotide sequence comprising at least 45% identity to the nucleotide set forth in SEQ ID NO: 1 and a nucleotide sequence encoding the amino acid sequence set forth in SEQ ID NO: 2.

The methods of the invention can be used to increase the level of unusual fatty acyl chains in oil extracted from a seed that synthesizes such fatty acyl chains during seed development. In engineering crop plants to produce specialty oils comprised of triacylglcerols with one or more unusual fatty acyl chains, scientists have encountered difficulties in achieving desired levels of such molecules in the oil. While it remains unclear why such molecules are not produced at the desired level, the unusual fatty acyl molecules may be preferentially shunted toward β-oxidation because such molecules are not generally preferred for esterification of glycerol skeletons in triacylglycerol biosynthesis. It is known that the first two acyltransferases in triacylglycerol biosynthesis have a rather narrow substrate specificity (Harwood (1996) *Biochim Biophys Acta* 1301:7–56), and thus, may act in vivo to limit the incorporation of unusual fatty acyl chains into triacylglycerols. The present invention does not depend on a particular biological mechanism, only that decreasing or increasing acyl-CoA thioesterase decreases β-oxidation.

The methods for decreasing β-oxidation increase the level of the desired unusual fatty acyl-CoA for triacylglycerol biosynthesis. An increased level of unusual fatty acyl chains in the developing seed increases the level of such acyl chains in triacylglycerol. In the presence of an increased level of unusual fatty acids, the enzyme diacylglycerol acyltransferase is known to take up these fatty acyl-CoAs and incorporate them into the sn-3 position of triacylglycerol. Thus, an increased level of an unusual fatty acyl chain can be achieved in seed oil.

In an embodiment of the invention, the level of unusual fatty acyl chains in the oil of a plant is increased. Any plant may be utilized that is capable of producing unusual fatty acyl chains in its seeds. Such a plant has been genetically engineered to produce the desired fatty acyl chain in its seeds or may be a plant that produces the desired fatty acyl chain in the absence of recombinant DNA in its genome. Preferably, such a plant is a crop plant, more preferably such a plant is crop plant that produces seeds that may be used for commercial oil production such as, for example, soybean, corn, Brassica, sunflower, safflower, peanut, cotton, flax, castor and palm. To increase the level of unusual fatty acyl chains in the seed oil, the plant can be transformed with an acyl-CoA thioesterase nucleotide sequence operably linked to a promoter that drives expression in the plant, particularly in the seeds of the plant.

Methods are provided for optimizing a plant for seed oil production. By "optimizing a plant for seed oil production" is intended that a plant is impacted in such a manner as to favorably affect seed oil accumulation. That is, seed oil accumulation is increased, at least one desired constituent of seed oil is increased, or a combination thereof. Thus, the methods find use in producing a plant that accumulates in its seeds a desired level of oil, a desired level of an oil constituent or both. Such a plant is desired for the extraction of standard vegetable oils or specialty oils. The methods involve decreasing β-oxidation by modulating acyl-CoA thioesterase expression as described supra and additionally decreasing the level or activity of at least one additional protein involved in β-oxidation in a plant seed.

The invention does not depend on a particular additional protein, only that decreasing or increasing the level or activity of such a protein in plant has a desired effect on seed oil accumulation in a plant. Generally, decreasing the level of such a protein will affect β-oxidation in a plant or tissue thereof. A protein that affects β-oxidation may be, for example, an enzyme in the β-oxidation pathway. Such enzymes include, but are not limited to, acyl-CoA oxidase, multifunctional protein type II, acyl-CoA synthetase, enoyl-CoA isomerase, β-ketoacyl-CoA thiolase and hydroxyacyl-CoA epimerase. Other proteins include, but are not limited to, catalase, malate dehydrogenase, carnatine acetyl transferase, citrate synthase, aconitase, isocitrate lyase, malate synthetase, and acyl-CoA thioesterase. Preferred proteins of the invention include acyl-CoA oxidase and multifunctional protein type II.

The level or activity of the additional protein may be decreased by any method known in the art. Such methods include, but are not limited to, cosuppression, antisense suppression and chimeraplasty. Preferably, the level or activity of the additional protein is decreased by transforming a plant with at least a portion of nucleotide construct that comprises a nucleotide sequence of a gene or transcript encoding the additional protein.

In producing high levels of seed oil, particularly seed oil comprised of unusual fatty acyl chains, further steps to decrease β-oxidation may be employed to achieve the desired level of oil. Because unusual fatty acyl-CoAs are not preferred as substrates by the acyltransferases that transfer fatty acyl chains to the glycerol moiety in triacylglycerol synthesis, such fatty acyl chains are preferentially shunted to β-oxidation in the developing seed. Decreasing β-oxidation in the developing seed can increase the pool of unusual fatty acyl chains available for triacylglycerol synthesis. It is known that in the presence of a high amount of unusual fatty acids, the enzyme diacylglycerol acyltransferase can incorporate such fatty acids into the sn-3 position of triacylglycerol. Thus, the methods of the invention can provide seeds that produce oil with higher levels of triacylglycerols with unusual fatty acyl chains.

In preferred methods of the invention that involve decreasing the level of at least one additional protein that affects β-oxidation, a plant or plant cell is transformed with a nucleotide construct comprising a promoter operably linked to nucleotide sequence encoding such an additional protein. Preferably, the nucleotide sequence comprises a coding sequence for an acyl-CoA thioesterase or a multifunctional protein type II. The methods of the invention additionally involve cosuppression or antisense suppression methods to decrease the level of at least one protein involved in β-oxidation.

To determine that the desired increase in the content of oil and/or triacylglycerols with the unusual fatty acyl chains has been achieved, oil may be extracted from seeds to determine total oil production and individual constituents of the oil may then be measured using any methods known to those of ordinary skill in the art.

The methods of the invention find use in increasing the level of unusual fatty acyl acids or constituents of oil comprising acyl chains of such fatty acids. By "unusual" fatty acids is intended fatty acids that have structural features such as, for example, an epoxy group, a triple bond, methyl branching or unusual carbon-chain length. Such "unusual" fatty acids include, but are not limited to, vernolic acid, petroselinic acid, sterculic acid, lesquerolic acid, densipolic acid, auricolic acid, cis-5-eicosenoic acid, cis-5-docosenoic acid, cis-5,13-docosdienoic acid, chaulmoogric acid, erucic acid, ricinoleic acid, labellenic acid, crepenynic acid and stearolic acid.

The invention also encompasses increasing the level of one or more of the acyltransferases that are involved in the biosynthesis of triacyiglycerol such as, for example, the diacyiglycerol acyltransferase from mouse (Accession No. AF078752, SEQ ID NO: 8). While the invention encompasses the use of any acyltransferase, preferred acyltransferases are those that have a wide substrate range. Of particular interest are acyltransferases that can efficiently catalyze the esterification of at least one unusual fatty acid to the glycerol moiety.

The invention is drawn to methods which increase the level of oil or a constituent thereof in a plant. Use of the term "oil" is not meant to limit the invention to fats or lipids that are liquid at room temperature, about 20° C. to 25° C. The oil of the present invention may or may not be liquid at room temperature. Generally, if the oil is solid at room temperature, heat may be applied to liquefy it.

The methods of the invention involve transforming a plant with a nucleotide construct. Such methods involve the nucleotide construct gaining access to the interior of a cell. The methods of the invention do not depend on a particular method for transforming a plant with a nucleotide construct, only that the nucleotide construct gains access to the interior of at least one cell of the plant. Methods for transforming plants are known in the art including, but not limited to, stable transformation methods and transient transformation methods By "stable transformation" is intended that the nucleotide construct that is introduced into a plant stably integrates into the genome of the plant is capable of being inherited by progeny thereof. By "transient transformation" is intended that a nucleotide construct that is introduced into a plant does not stably integrate into the genome of the plant.

In certain embodiments of the invention, a plant cell is transformed with at least one nucleotide construct comprising a nucleotide sequence encoding an acyl-CoA thioesterase, or other protein affecting β-oxidation, operably linked in a sense or antisense orientation to a promoter that drives expression in a plant cell. Preferably, such a transformed plant cell is regenerated into a stably transformed plant, wherein the nucleotide construct is stably incorporated into the genome of the transformed plant.

The methods of the invention also encompass the use of the nucleotide constructs of the invention in methods for altering or mutating any genomic nucleotide sequence in an organism, such as, for example, chimeraplasty. Thus, the methods of the invention may involve modulating acyl-CoA thioesterases genes and as well as other genes which might affect β-oxidation in a plant. Any part of gene may be altered including, but not limited to, nucleotide sequences of exons, introns, untranscribed regions of genes, regions corresponding to untranslated and regions of a transcript. For example, chimeraplasty may be used with an acyl-CoA nucleotide sequence to increase or decrease acyl-CoA thioesterase expression in a plant by altering a coding sequence in the genome of the plant in such a manner that the amino acid sequence of the encoded acyl-CoA is changed.

Compositions of the invention include nucleotide sequences that encode acyl-CoA thioesterases that are involved in β-oxidation. In particular, the present invention provides for isolated nucleic acid molecules comprising nucleotide sequences encoding the amino acid sequences shown in SEQ ID NO: 2. Further provided are polypeptides having an amino acid sequence encoded by a nucleic acid molecule described herein, for example those set forth in SEQ ID NO: 1, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological of the native protein and hence retain acyl-CoA thioesterase activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an acyl-CoA thioesterase nucleotide sequence that encodes a biologically active portion of an acyl-CoA thioesterase of the invention will encode at least 15, 25, 30, 50, 100, 150, 200, or 240 contiguous amino acids, or up to the total number of amino acids present in a full-length acyl-CoA thioesterase of the invention (for example, 242 amino acids for SEQ ID NO: 2). Fragments of an acyl-CoA thioesterase nucleotide sequence that are useful as hybridization probes or PCR primers generally need not encode a biologically active portion of an acyl-CoA thioesterase.

Thus, a fragment of an acyl-CoA thioesterase nucleotide sequence may encode a biologically active portion of an acyl-CoA thioesterase, or it may be a fragment that can be used as a hybridization probe or PCR primer using methods disclosed below. A biologically active portion of an acyl-CoA thioesterase can be prepared by isolating a portion of one of the acyl-CoA thioesterase nucleotide sequences of the invention, expressing the encoded portion of the acyl-CoA thioesterase (e.g., by recombinant expression in vitro), and assessing the activity of the encoded portion of the acyl-CoA thioesterase. Nucleic acid molecules that are fragments of an acyl-CoA thioesterase nucleotide sequence comprise at least 16, 20, 50, 75, 100, 150, 200, 250, 300, 350, 400, 450, 500, 550, 600, 650, 700, 800, 900, 1,000, or 1,100 nucleotides, or up to the number of nucleotides present in a full-length acyl-CoA thioesterase nucleotide sequence disclosed herein (for example, 1169 nucleotides for SEQ ID NO: 1)

By "variants" is intended substantially similar sequences. For nucleotide sequences, conservative variants include those sequences that, because of the degeneracy of the genetic code, encode the amino acid sequence of one of the acyl-CoA thioesterase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an the acyl-CoA thioesterase protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, the acyl-CoA thioesterase activity as described herein. Such variants may result from, for example, genetic polymorphism or from human manipulation. Biologically active variants of a native the acyl-CoA thioesterase protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the acyl-CoA thioesterase can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired acyl-CoA thioesterase activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying acyl-CoA thioesterase activity. See, for example, Jones et al. ((1999) *J Biol Chem.* 274:9216–9223), herein incorporated by reference.

Variant nucleotide sequences and proteins also encompass sequences and proteins derived from a mutagenic and recombinogenic procedure such as DNA shuffling. With such a procedure, one or more different acyl-CoA thioesterase coding sequences can be manipulated to create a new acyl-CoA thioesterase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the acyl-CoA thioesterase gene of the invention and other known acyl-CoA thioesterase genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequence set forth herein. Sequences isolated based on their sequence identity to the entire acyl-CoA thioesterase sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the acyl-CoA thioesterase nucleotide sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire acyl-CoA thioesterase nucleotide sequence disclosed herein, or one or more portions thereof, may be used as a probe capable of specifically hybridizing to corresponding acyl-CoA thioesterase nucleotide sequences [and messenger RNAs]. To achieve specific hybridization under a variety of conditions, such probes include sequences that are unique among acyl-CoA thioesterase nucleotide sequences and are preferably at least about 10 nucleotides in length, and most preferably at least about 20 nucleotides in length. Such probes may be used to amplify corresponding acyl-CoA thioesterase nucleotide sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1×to 2×SSC (2×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.$+16.6$ (log M)$+0.41$ (% GC) $-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an acyl-CoA thioesterase and which hybridize under stringent conditions to the acyl-CoA thioesterase nucleotide sequence disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. The nucleotide constructs, nucleotide molecules and nucleotide sequences of the invention additionally encompass all complementary forms of such constructs, molecules and sequences. Further, the nucleotide constructs, nucleotide molecules and nucleotide sequences of the present invention encompass all nucleotide constructs, molecules and sequences which can be employed in the methods of the present invention for transforming plants including, but not limited to, those comprised of deoxyribonucleotides, ribonucleotides and combinations thereof. Such deoxyribonucleotides and ribonucleotides include both naturally occurring molecules and synthetic analogues. The nucleotide constructs, nucleotide molecules and nucleotide sequences of the invention also encompass all forms of nucleotide constructs including, but not limited to, single-stranded forms, double-stranded forms, hairpins, stem-and-loop structures and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In various embodiments of the invention, the genome of a plant is altered following the introduction of the nucleotide construct into a cell. For example, the nucleotide construct, or any part thereof, may incorporate into the genome of the plant. Alterations to the genome of the present invention include, but are not limited to, additions, deletions and substitution of nucleotides in the genome. While the methods of the present invention do not depend on additions, deletions, or substitutions of any particular number of nucleotides, it is recognized that such additions, deletions or substitutions comprise at least one nucleotide.

The nucleotide constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821 and Beetham et al (1999) *Proc. Natl. Acad. Sci. USA* 96:8774–8778; herein incorporated by reference.

If necessary, an acyl-CoA thioesterase or other protein may be modified to direct the protein to the peroxisomes of a plant. Methods for directing a protein to the peroxisome are well known in the art. Typically, such methods involve operably linking a nucleotide sequence encoding a peroxisome-targeting signal to the coding sequence of the protein or modifying the coding sequence of the protein to additionally encode the peroxisome-targeting signal without substantially affecting the intended function of the encoded protein. See, for example, Olsen et al. (1993) *Plant Cell* 5:941–952, Mullen et al. (1997) *Plant Physiol.* 115:881–889, Gould et al. (1990) *EMBO J.* 9:85–90, Flynn et al. (1998) *Plant J.* 16:709–720; Preisig-Muller and Kindl (1993) *Plant Mol Biol.* 22:59–66 and Kato et al. (1996) *Plant Cell* 8:1601–1611; herein incorporated by reference.

It is recognized that an protein of the invention may be directed to the peroxisome by operably linking a peroxisome-targeting signal to the C-terminus or the N-terminus of the protein. It is further recognized that an protein which is synthesized with a peroxisome-targeting signal may be processed proteolytically in vivo resulting in the removal of the peroxisome-targeting signal from the amino acid sequence of the mature, peroxisome-localized protein.

The acyl-CoA thioesterase nucleotide sequences of the invention are provided in expression cassettes for expression in the plant of interest. The cassette will include 5' and 3' regulatory sequences operably linked to an acyl-CoA thioesterase nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of protein coding sequences, "operably linked" includes joining two protein coding sequences in such a manner that both sequences are in the same reading frame for translation. For example, a nucleotide sequence encoding a peroxisome-targeting signal may be joined to the 3' end of a coding sequence of a protein of the invention in such manner that both sequences are in the same reading frame for translation to yield a the protein of the invention with a C-terminal addition of the peroxisome-targeting signal.

The expression cassette may additionally contain at least one additional gene to be cotransformed into the organism. Alternatively, the additional gene(s) can be provided on multiple expression cassettes.

Such an expression cassette is provided with a plurality of restriction sites for insertion of the acyl-CoA thioesterase nucleotide sequence to be under the transcriptional regulation of the regulatory regions. The expression cassette may additionally contain selectable marker genes.

The expression cassette will include in the 5'-3' direction of transcription, a transcriptional and translational initiation region, an acyl-CoA thioesterase DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of acyl-CoA thioesterase in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced acyl-CoA thioesterase expression within a particular plant tissue. Tissue-preferred promoters include Yamamoto et al. (1997) *Plant J.* 12(2)255–265; Kawamata et al. (1997) *Plant Cell Physiol.*38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

Leaf-preferred promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2): 207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a βglucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2) :343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4) :759–772); and rolB promoter (Capana et al. (1994) *Plant Mol. Biol.* 25(4):681–691. See also U.S. Pat. Nos. 5,837, 876; 5,750,386; 5,633,363; 5,459,252; 5,401,836; 5,110, 732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. application Ser. No. 60/097,233, filed Aug. 20, 1998, herein incorporated by reference). Gama-zein is a preferred endosperm-preferred promoter. Glob-1 is a preferred embryo-preferred promoter. For dicots, seed-preferred promoters include, but are not limited to, bean βphaseolin, napin, βconglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506–511; Christopherson et al. (1992) Proc. Natl. Acad. Sci. USA 89:6314–6318; Yao et al. (1992) Cell 71:63–72; Reznikoff (1992) Mol. Microbiol. 6:2419–2422; Barkley et al. (1980) in The Operon, pp. 177–220; Hu et al. (1987) Cell 48:555–566; Brown et al (1987) Cell 49:603–612; Figge et al. (1988) Cell 52:713–722; Deuschle et al. (1989) Proc. Natl. Acad. Aci. USA 86:5400–5404; Fuerst et al. (1989) Proc. Natl. Acad. Sci. USA 86:2549–2553; Deuschle et al. (1990) Science 248:480–483; Gossen (1993) Ph.D. Thesis, University of Heidelberg; Reines et al. (1993) Proc. Natl. Acad. Sci. USA 90:1917–1921; Labow et al. (1990) Mol. Cell. Biol. 10:3343–3356; Zambretti et al. (1992) Proc. Natl. Acad. Sci. USA 89:3952–3956; Baim et al. (1991) Proc. Natl. Acad. Sci. USA 88:5072–5076; Wyborski et al. (1991) Nucleic Acids Res. 19:4647–4653; Hillenand-Wissman (1989) Topics Mol. Struc. Biol. 10:143–162; Degenkolb et al. (1991) Antimicrob. Agents Chemother. 35:1591–1595; Kleinschnidt et al. (1988) Biochemistry 27:1094–1104; Bonin (1993) Ph.D. Thesis, University of Heidelberg; Gossen et al. (1992) Proc. Natl. Acad. Sci. USA 89:5547–5551; Oliva et al. (1992) Antimicrob. Agents Chemother. 36:913–919; Hlavka et al. (1985) Handbook of Experimental Pharmacology, Vol. 78 (Springer-Verlag, Berlin); Gill et al. (1988) Nature 334:721–724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320–334), electroporation (Riggs et al. (1986) Proc. Natl. Acad. Sci. USA 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) EMBO J. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soybean); McCabe et al. (1988) Biol/Technology 6:923–926 (soybean); Finer and McMullen (1991) In Vitro Cell Dev. Biol. 27P:175–182 (soybean); Singh et al. (1998) Theor. AppL. Genet. 96:319–324 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad. Sci. USA 84:5345–5349 (Liliaceae); De Wet et al. (1985) in The Experimental Manipulation of Ovule Tissues, ed. Chapman et al. (Longman, N.Y.), pp. 197–209 (pollen); Kaeppler et al. (1990) Plant Cell Reports 9:415–418 and Kaeppler et al. (1992) Theor. Appl. Genet. 84:560–566 (whisker-mediated transformation); D'Halluin et al. (1992) Plant Cell 4:1495–1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed may be grown into plants in accordance with conventional ways. See, for example, McCormick et al (1986) Plant Cell Reports 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

A plant can also be transformed with an acyl-CoA thioesterase nucleotide construct or other nucleotide construct of the invention by contacting the plant with a virus or viral nucleic acids. Generally, such methods involve incorporating the nucleotide construct of interest within a viral DNA or RNA molecule. It is recognized that the an acyl-CoA thioesterase of the invention may be initially synthesized as part of a viral polyprotein which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein involving viral DNA or RNA molecules are known in the art. See, for example, U.S. Pat. Nos. 5,889,191, 5,889,190, 5,866,785, 5,589,367 and 5,316,931; herein incorporated by reference.

It is recognized that with these nucleotide sequences, antisense constructions, complementary to at least a portion of the messenger RNA (mRNA) for the acyl-CoA thioesterase sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation, often referred to as cosuppression methods, are known in the art. Such methods may be referred to methods The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

In the practice of certain specific embodiments of the present invention, a plant or cell thereof may be transformed with two or more nucleotide constructs. Those of ordinary skill in the art realize that this can be accomplished in any one of a number of ways. For example, each of the respective nucleotide constructs may be introduced into a cell, or the constructs may be ligated together to form-i a single construct and then used to transform a cell. Alternatively, separate cell can be transformed with each of the separate constructs containing one or a subset of the desired nucleotide constructs. Transformed plants that posses the desired transgenic phenotype can be regenerated and then selected by standard methods available in the art such as, for example, assaying enzyme activities, immunoblotting using antibodies which bind to the enzymes of interest, assaying for the products of a reporter or marker gene, and the like. Then, all of the desired nucleotide constructs can be brought together into a single plant through one or more rounds of cross pollination utilizing the previously selected transformed plants as parents.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of desired nucleotide constructs of the parental plants can be selected from the progeny by standard methods available in the art as described supra for selecting transformed plants. If necessary, the selected progeny can be used as either the pollen donor or pollen recipient in a subsequent cross pollination.

The present invention may be used for transformation of any plant species, including, but not limited to, corn (*Zea mays*), *Brassica* spp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (Setaria italica), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Plants of particular interest include grain plants that provide seeds of interest, oilseed plants, and leguminous plants. Seeds of interest include grain seeds, such as maize (corn), wheat, barley, rice, sorghum, rye, etc. Oilseed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc. Preferably, plants of the present invention are crop plants (for example, corn, soybean, rice, sunflower, *Brassica*, safflower, peanut, sorghum, wheat, cotton, millet, tobacco, alfalfa, etc.), more preferably corn and soybean plants, yet more preferably corn plants.

The allosteric effectors and enzyme inhibitors of the invention can be administered to a plant in an effective amount by, for example, injecting, infusing, pipeting, spraying, atomizing, dusting, scattering, coating or pouring, introducing into or on the soil, introducing into irrigation water, by seed treatment or general application or dusting at any time. By "effective amount" is intended an amount that, when administered to a plant, produces the desired decrease or increase in acyl-CoA thioesterase activity.

Oil or oil constituents can be measured by any method known in the art. In order to make a determination of the amount of oil in seeds and/or the amount of specific fatty acids present in the oil and their respective concentrations, mature seeds can be crushed (e.g., in a hydraulic press), and the endogenous oil can be readily extracted with hexane or by other suitable techniques in accordance with procedures known in the art. Similarly, any plant tissue can be ground or crushed and then extracted with hexane to recover oil. The hexane can be separated from the oil by evaporation, and the amount of oil remaining determined. The fatty acids can be determined following transmethylation. The resulting methyl esters of the fatty acids can be separated, and their concentrations determined by use of capillary gas chromatography in accordance with standard operating procedures known in the art. For example, a Hewlett-Packard 5890 gas chromatograph and a 7673 autosampler with a flame ionization detector can be utilized. The data can be collected and integrated using Perkin Elmer software in conjunction with Perkin Elmer interfaces. The integrated areas of the peaks corresponding to the methyl esters of the various fatty acids can be grouped and normalized to yield their relative abundances. See "Automating Fatty Acid Analyses From Seeds" by Thomas B. Brumback, Jr. et al., Chemiometrics and Intelligent Laboratory Systems: Laboratory Information Management, Vol.21, Page 215 to 222 (1993). Other analytical techniques similarly can be utilized that are known to yield reliable results, such as the American Oil Chemists Society (AOCS) Official Method Ce 1e-91.

The following examples are presented by way of illustration, not by way of limitation.

EXPERIMENTAL

EXAMPLE 1

Manipulating Oil Biosynthesis and Oil Accumulation in Plants

Acyl-CoA thioesterases catalyze the hydrolysis of acyl-CoA to free fatty acids and CoA. They are found in the cytosol, mitochondria, and peroxisomes in yeast and animal cells (Smith (1994) *FASEB J* 8:1248–1259). The peroxisomal acyl-CoA thioesterase (PTE) has been implicated in fatty acid β-oxidation in yeast because loss of this gene interferes with the ability of yeast to grow on fatty acids (Jones et al. (1999) *J. Biol. Chem.* 274:9216–9223). Moreover, overexpression of this gene in yeast also leads to reduced β-oxidation (Chang et al. (1999) *J. Cell Sci.* 112:1579–1590). Cosuppression and/or overexpression of this gene in plant cells would likely change the β-oxidation rate and thereby reduce the flux of fatty acids through peroxisome.

A cDNA (SEQ ID NO: 1) of maize homolog to the yeast PTE gene has been identified. A nucleotide construct comprising a nucleotide sequence of the invention operably linked to the oleosin promoter has been introduced into maize plants for the following objectives. First, this gene is useful in the production of unusual fatty acids such as vernolate in plants. Vernolate-producing *Arabidopsis* lines have been reported to have a greater flux of fatty acids through the peroxisomes, which may account for the relatively low level (<3% seed weight) accumulation of this fatty acid in mature seeds. By reducing the peroxisomal β-oxidation rate during seed development, higher levels of the novel fatty acid can be accumulated. Second, a lower rate of β-oxidation in seed crops during seed maturation can increase the overall oil accumulation.

Unusual fatty acids such as epoxy (vernolate) and hydroxy (ricinoleic) fatty acids have a wide range of industrial applications (Gunstone et al. (1994) *The Lipid Handbook*, Chapman & Hall, London). Previous transgenic approaches to producing large quantities of these fatty acids in high-yield grain crops encountered low-level accumulation of the desired fatty acid, and thus were not economically viable. The limitation placed on non-natural fatty acid accumulation in these crops may stem from the fact that the acyltransferases for triacylglycerol (TAG) synthesis prefer the natural fatty acyl-CoAs to the unusual fatty acyl-CoA. It is well established that at least the first two acyltransferases in TAG biosynthesis have rather narrow substrate specificity (Harwood (1996) *Biochim Biophys Acta* 1301:7–56). Inefficient incorporation of the unusual fatty acid would then lead to increased flux of these fatty acids through the peroxisome to recycle the carbon for the synthesis of natural fatty acids. One way to overcome this is to reduce the β-oxidation rate in plant cells and thereby increase the proportion of the desired fatty acyl-CoA in the acyl-CoA pool for TAG synthesis. In the presence of a high amount of unusual fatty acids, the acyltransferases would be forced to utilize such fatty acids, resulting in a higher levels of accumulation of such fatty acids in mature seeds.

The peroxisomal acyl-CoA thioesterase is believed to regulate the CoA pool in peroxisomes. Fatty acids must be esterified with CoA before their βoxidation. However, if CoA is appended to poorly metabolized or nonmetabolizable fatty acids, CoASH levels would fall as more and more CoA is incorporated into these metabolic sinks. Peroxisomal acyl-CoA thioesterase serves to liberate the CoASH from these dead-end molecules (Chang et al. (1999) *J. Cell Sci.* 112:1579–1590). The liberated CoASH will be used to activate other fatty acids, while the released fatty acid will be free to equilibrate with cellular and extracellular pools, reducing their concentration in the peroxisome. Experimental evidence has shown that loss of function or overexpression of a PTE gene leads to reduction in β-oxidation and peroxisome abundance. A PTE nucleotide sequence of the invention operably linked to a seed-preferred promoter can be used to transform *Arabidopsis* plants that produce vernolate in their seeds. Expressing this PTE gene in a seed-specific manner in vernolate-producing *Arabidopsis* plants can lead to increased PTE which can inhibit fatty acid oxidation by eliminating acyl-CoA substrates. The increased concentration of the desired fatty acid in the endoplasmic reticulum (ER) would shift the equilibrium to making TAG with enhanced contents of unusual fatty acids.

When expressed in maize, PTE can sevo the same function to break up the acyl-CoA substrates of β-oxidation. The normal flux of fatly acids through peroxisomes would then be re-equilibrated into other cellular pools. At least a portion of these fatty acids are expected to be directed to the synthesis of TAG in the ER. A number of other genes can also be used in combination with PTE. They include the acyl-CoA oxidase and the multifunctional protein type II. These proteins exert metabolic control on β-oxidation and peroxisome abundance (Chang et al. (1999) *J. Cell Sci.* 112:1579–1590). Cosuppression of the genes encoding one or both of these proteins can inhibit fatty acid β-oxidation and increase the fatty acid flux toward the biosynthesis of TAG resulting in maize kernels with an increased content of oil.

EXAMPLE 2

Transformation and Regeneration of Transgenic Maize Plants by Particle Bombardment Immature maize embryos from greenhouse donor plants are bombarded with a plasmid containing the acyl-CoA thioesterase nucleotide sequence of the invention operably linked to a oleosin promoter plus a plasmid containing the selectable marker gene PAT (Wohlleben et al. (1988) *Gene* 70:25–37) that confers resistance to the herbicide Bialaphos. Transformation is performed as follows. Media recipes follow below.

Preparation of Target Tissue

Immature embryos from F1 hybrid plants of the Hill genotype (Armstrong et al. (1991) *Maize Genet. Coop. Newslett.* 65:92–93) are isolated 8–10 days after pollination at 1.2–1.8 mm in length. The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the acyl-CoA thioesterase nucleotide sequence of the invention operably linked to a oleosin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Bombardment and Culture Media

Bombardment medium (560Y) comprises 4.0 g/l 1N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117–074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Particle Gun Treatment

The sample plates are bombarded at level #4 in particle gun #HE34–1 or #HE34–2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for altered acyl-CoA thioesterase activity and/or altered oil content in kernels.

EXAMPLE 3

*Agrobacterium*-Mediated Transformation of Maize

For *Agrobacterium*-mediated transformation of maize with an acyl-CoA thioesterase nucleotide sequence of the invention operably linked to a oleosin promoter, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the the acyl-CoA thioesterase nucleotide sequence to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 4

Production of Transgenic Soybean by Embryo Transformation

Soybean embryos are bombarded with a plasmid containing an acyl-CoA thioesterase nucleotide sequence of the invention operably linked to a oleosin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the acyl-CoA thioesterase nucleotide sequence of the invention operably linked to a oleosin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 5

Production of Transgenic Sunflower by Meristem Tissue Transformation

Sunflower meristem tissues are transformed with an expression cassette containing an acyl-CoA thioesterase nucleotide sequence of the invention operably linked to a oleosin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minn. Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to Agrobacterium treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the acyl-CoA thioesterase nucleotide sequence of the invention operably linked to a oleosin promoter is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_{b\ 4}$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for acyl-CoA thioesterase activity.

NPTII-positive shoots are grafted to Pioneer® hybrid 6440 in vitro-grown sunflower seedling rootstock. Surface sterilized seeds are germinated in 48–0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by acyl-CoA thioesterase activity analysis of leaf extracts while transgenic seeds harvested from NPTII-positive $T_0$ plants are identified by acyl-CoA thioesterase activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 $\mu$m tungsten particles are resuspended in 150 $\mu$l absolute ethanol. After sonication, 8 $\mu$l of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 $\mu$l/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 $\mu$g/ml cefotaxime). The plantlets are cultured on the medium for about two weeks under 16-hour day and 26° C. incubation conditions.

Explants (around 2 cm long) from two weeks of culture in 374C medium are screened for acyl-CoA thioesterase activity using assays known in the art [add references to known assays if at all possible]. After positive (i.e., for increased or decreased acyl-CoA thioesterase activity expression) explants are identified, those shoots that fail to exhibit the desired acyl-CoA thioesterase activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for the desired acyl-CoA thioesterase expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for decreasing β-oxidation in a plant or plant part comprising introducing into said plant or plant part a nucleotide construct comprising a promoter operably linked to an acyl-CoA thioesterase nucleotide sequence, wherein said promoter drives expression in a plant cell, and said nucleotide sequence is selected from the group consisting of:
   (a) the nucleotide sequence set forth in SEQ ID NO: 1;
   (b) a nucleotide sequence which encodes a polypeptide comprising the amino acid sequence set forth in SEQ NO: 2;
   (c) a nucleotide sequence comprising at least 95% identity to the nucleotide sequence set forth in SEQ ID NO: 1, wherein said nucleotide sequence encodes a polypeptide having acyl-CoA thioesterase activity; and
   (d) the nucleotide sequence that is fully complementary to the nucleotide sequence of (a), (b), or (C);
   wherein the level of acyl-CoA thioesterase is increased and the level of oil or the level of at least one oil constituent is increased in said plant or at least one part of said plant, thereby decreasing β-oxidation in the plant, and wherein said part is selected from the group consisting of a fruit, a seed, and an embryo.

2. The method of claim 1, wherein said part is a seed or an embryo.

3. The method of claim 1, wherein said acyl-CoA thioesterase is peroxisomal acyl-CoA thioesterase.

4. The method of claim 1, wherein said promoter is selected from the group consisting of seed-preferred, constitutive, chemically regulatable and developmentally regulated promoters.

5. The method of claim 1, wherein said nucleotide construct further comprises an operably linked nucleotide sequence encoding a peroxisome-targeting signal.

6. The method of claim 1, wherein said oil constituent comprises a fatty acid selected from the group consisting of vernolic acid, petroselinic acid, sterculic acid, lesquerolic acid, densipolic acid, auricolic acid, cis-5-eicosenoic acid, cis-5-docosenoic acid, cis-5,13-docosdienoic acid, chaulmoogric acid, erucic acid, ricinoleic acid, labellenic acid, crepenynic acid and stearolic acid.

7. The method of claim 1 further comprising regenerating said cell into a transformed plant.

8. The method of claim 1, wherein said plant is stably transformed with said nucleotide construct.

9. The method of claim 1, wherein said nucleotide construct is incorporated within a viral DNA or RNA molecule.

10. The method of claim 9, wherein said introducing comprises contacting the plant with a virus or viral nucleic acids.

11. A transformed plant expressing a stably incorporated nucleotide construct in its genome comprising a promoter that drives expression in a plant operably linked to a nucleotide sequence encoding an acyl-CoA thioesterase, said nucleotide sequence selected from the group consisting of:
   (a) the nucleotide sequence set forth in SEQ ID NO: 1;
   (b) a nucleotide sequence comprising at least 95% identity to the nucleotide sequence set forth in SEQ ID NO: 1, wherein said nucleotide sequence encodes a polypeptide having acyl-CoA thioesterase activity; and
   (c) the nucleotide sequence that is fully complementary to the nucleotide sequence of (a) or (b);
   wherein the level of acyl-CoA thioesterase is increased in said plant or at least one part of said plant, said part selected from the group consisting of a fruit, a seed, and an embryo.

12. The plant of claim 11, wherein said acyl-CoA thioesterase is a peroxisomal acyl-CoA thioesterase.

13. The plant of claim 11, wherein said plant produces at least one unusual fatty acyl chain in its seeds, wherein said fatty acyl chain comprises a fatty acid selected from the group consisting of vernolic acid, petroselinic acid, sterculic acid, lesquerolic acid, densipolic acid, auricolic acid, cis-5-eicosenoic acid, cis-5-docosenoic acid, cis-5,13-docosdienoic acid, chaulmoogric acid, erucic acid, ricinoleic acid, labellenic acid, crepenynic acid and stearolic acid.

14. The plant of claim 11, wherein said plant is a monocot.

15. The plant of claim 14, wherein said monocot is selected from the group consisting of maize, wheat, rice, sorghum, barley, miller, rye and pulm.

16. The plant of claim 11, wherein said plant is a dicot.

17. The plant of claim 16, wherein said dicot is selected from the group consisting of soybean, *Brassica*, alfalfa, safflower, sunflower, cotton, flax, peanut and potato.

18. Transformed seed of the plant of claim 11.

19. A transformed plant cell expressing a stably incorporated nucleotide construct in its genome comprising a promoter that drives expression in a plant operably linked to a nucleotide sequence encoding an acyl-CoA thioesterase, said nucleotide sequence selected from the group consisting of:
   (a) the nucleotide sequence set forth in SEQ ID NO: 1;
   (b) a nucleotide sequence comprising at least 95% identity to the nucleotide sequence set forth in SEQ ID NO: 1, wherein said nucleotide sequence encodes a polypeptide having acyl-CoA thioesterase activity; and
   (c) the nucleotide sequence that is fully complementary to the nucleotide sequence of (a) or (b);
   wherein the level of acyl-CoA thioesterase is increased in said plant cell.

* * * * *

UNITED STATES PATENT AND TRADEMARK OFFICE
CERTIFICATE OF CORRECTION

PATENT NO. : 6,914,170 B2
DATED : July 5, 2005
INVENTOR(S) : Li et al.

It is certified that error appears in the above-identified patent and that said Letters Patent is hereby corrected as shown below:

Column 37,
Line 18, "(C)" should read -- (c) --;
Lines 39 and 40, "cis-5", should read -- *cis*-5 --.

Column 38,
Line 30, "pulm" should read -- palm --.

Signed and Sealed this

Twenty-seventh Day of September, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 1169
<212> TYPE: DNA
<213> ORGANISM: Zea mays
<220> FEATURE:
<221> NAME/KEY: CDS
<222> LOCATION: (89)..(814)

<400> SEQUENCE: 1

```
gagctccacc gcggtggcgg ccgctctaga actagtggat ccccogggct gcaggaattc      60 ggcacgagag actgttgatt gtctaaaa atg gtg cat agt ttg cat gca att       112
                                Met Val His Ser Leu His Ala Ile
                                 1               5 ttt ctt gtt gct gga gac aat aac ata ccg ata ata tat caa gtt cat      160
Phe Leu Val Ala Gly Asp Asn Asn Ile Pro Ile Ile Tyr Gln Val His
    10                  15                  20 cgg gca cgt gat gga tcc agc ttt gcc aca aga aaa gtg gag gca aag      208
Arg Ala Arg Asp Gly Ser Ser Phe Ala Thr Arg Lys Val Glu Ala Lys
25                  30                  35                  40 cag aag ggc cta gtt gta ttc acc ttg att gct tct ttc cag aag gaa      256
Gln Lys Gly Leu Val Val Phe Thr Leu Ile Ala Ser Phe Gln Lys Glu
                45                  50                  55 gaa gtg ggt ttt gag cat cag gct gca atc atg cct gat gtt cct ccg      304
Glu Val Gly Phe Glu His Gln Ala Ala Ile Met Pro Asp Val Pro Pro
            60                  65                  70 cca gaa cag ctc ctt aat ctg gag gag ata cgt gaa aga cgg ctt act      352
Pro Glu Gln Leu Leu Asn Leu Glu Glu Ile Arg Glu Arg Arg Leu Thr
        75                  80                  85 gat cca cgc ttc cca tcc caa tat agg aac ttg gca gct aaa aaa aag      400
Asp Pro Arg Phe Pro Ser Gln Tyr Arg Asn Leu Ala Ala Lys Lys Lys
    90                  95                  100 ttt att cct tgg ccc ata gaa atg aga ttt tgt gaa ggt tca gcg tct      448
Phe Ile Pro Trp Pro Ile Glu Met Arg Phe Cys Glu Gly Ser Ala Ser
105                 110                 115                 120 caa cat aaa cca agc tta aac tac tgg ttt aga gct cga ggg aaa ctc      496
Gln His Lys Pro Ser Leu Asn Tyr Trp Phe Arg Ala Arg Gly Lys Leu
                125                 130                 135 tca gac gac caa gct cta cac aga tgt gtt gta gca tat gct tcg gat      544
Ser Asp Asp Gln Ala Leu His Arg Cys Val Val Ala Tyr Ala Ser Asp
            140                 145                 150 cta cta ttt tct ggg gtg agc ctt aac cct cat cgg gag aag ggt ttg      592
Leu Leu Phe Ser Gly Val Ser Leu Asn Pro His Arg Glu Lys Gly Leu
        155                 160                 165 aag aca tac tgc ctc agt ctt gac cat tcc atc tgg ttc cac aaa cct      640
Lys Thr Tyr Cys Leu Ser Leu Asp His Ser Ile Trp Phe His Lys Pro
    170                 175                 180 gtg aag gct gac gaa tgg atg ctg tat gtg atc gag agc cca tct gcg      688
Val Lys Ala Asp Glu Trp Met Leu Tyr Val Ile Glu Ser Pro Ser Ala
185                 190                 195                 200 cac ggt ggt cgc ggt ttc gtc acc gga cgc atg ttc aac agg caa gga      736
His Gly Gly Arg Gly Phe Val Thr Gly Arg Met Phe Asn Arg Gln Gly
                205                 210                 215
```

```
gag ctt atc atg tcg ctg acc caa gag gca ttg att cga agg gag aag      784
Glu Leu Ile Met Ser Leu Thr Gln Glu Ala Leu Ile Arg Arg Glu Lys
        220                 225                 230 ccg cga gga cca aat ccg agg ccg aag ctt tgaggcacct gacagcctct        834
Pro Arg Gly Pro Asn Pro Arg Pro Lys Leu
        235                 240 gcagtcgact gtagaggatc ccaaccgagc tttgagaggc gcaccatcct ttcttctaat    894
ttggtttaga tatttatgaa ttcacaaaca aaaatataga atatcaagca gtataaaaga    954
tctcaagtca aacctaacat tttttttcat ttctccggat gatttctatt tgttttggtg   1014
tgtgtgtggt tggaggggta ttggaagcgg aagcggaggc ggagggtttg atactttagg   1074
ctatttcctg cagcttactt tcattatacg aacagtatat atacatattt aaacttcaaa   1134
aaaaaaaaaa aaaactcgag gggggcccg gtacc                               1169
```

<210> SEQ ID NO 2
<211> LENGTH: 242
<212> TYPE: PRT
<213> ORGANISM: Zea mays

<400> SEQUENCE: 2

```
Met Val His Ser Leu His Ala Ile Phe Leu Val Ala Gly Asp Asn Asn
  1               5                  10                  15

Ile Pro Ile Ile Tyr Gln Val His Arg Ala Arg Asp Gly Ser Ser Phe
             20                  25                  30

Ala Thr Arg Lys Val Glu Ala Lys Gln Lys Gly Leu Val Val Phe Thr
         35                  40                  45

Leu Ile Ala Ser Phe Gln Lys Glu Glu Val Gly Phe Glu His Gln Ala
     50                  55                  60

Ala Ile Met Pro Asp Val Pro Pro Glu Gln Leu Leu Asn Leu Glu
 65                  70                  75                  80

Glu Ile Arg Glu Arg Arg Leu Thr Asp Pro Arg Phe Pro Ser Gln Tyr
                 85                  90                  95

Arg Asn Leu Ala Ala Lys Lys Phe Ile Pro Trp Pro Ile Glu Met
            100                 105                 110

Arg Phe Cys Glu Gly Ser Ala Ser Gln His Lys Pro Ser Leu Asn Tyr
        115                 120                 125

Trp Phe Arg Ala Arg Gly Lys Leu Ser Asp Asp Gln Ala Leu His Arg
    130                 135                 140

Cys Val Val Ala Tyr Ala Ser Asp Leu Leu Phe Ser Gly Val Ser Leu
145                 150                 155                 160

Asn Pro His Arg Glu Lys Gly Leu Lys Thr Tyr Cys Leu Ser Leu Asp
                165                 170                 175

His Ser Ile Trp Phe His Lys Pro Val Lys Ala Asp Glu Trp Met Leu
            180                 185                 190

Tyr Val Ile Glu Ser Pro Ser Ala His Gly Gly Arg Gly Phe Val Thr
        195                 200                 205

Gly Arg Met Phe Asn Arg Gln Gly Glu Leu Ile Met Ser Leu Thr Gln
    210                 215                 220

Glu Ala Leu Ile Arg Arg Glu Lys Pro Arg Gly Pro Asn Pro Arg Pro
225                 230                 235                 240

Lys Leu
```